United States Patent [19]
Kroll

[11] Patent Number: 5,772,690
[45] Date of Patent: Jun. 30, 1998

[54] SYSTEM HAVING A SURROGATE DEFIBRILLATION ELECTRODE FOR TESTING IMPLANTABLE CARDIOVERTER-DEFIBRILLATORS DURING IMPLANT

[75] Inventor: Mark W. Kroll, Simi Valley, Calif.

[73] Assignee: Pacesetter, Inc., Sylmar, Calif.

[21] Appl. No.: 738,953

[22] Filed: Oct. 24, 1996

[51] Int. Cl.⁶ .................................................. A61N 1/372
[52] U.S. Cl. .................................................................. 607/7
[58] Field of Search .................................. 607/5, 7, 8, 4, 607/142

[56] References Cited

U.S. PATENT DOCUMENTS

| | | | |
|---|---|---|---|
| 5,107,834 | 4/1992 | Ideker et al. ................................ | 607/5 |
| 5,433,730 | 7/1995 | Alt ............................................... | 607/5 |

OTHER PUBLICATIONS

Sanjeev Saksena et al., "Low–Energy Endocardial Defibrillation Using an Axillary or a Pectoral Thoracic Electrode Location," *Circulation*, vol. 88, No. 6, pp. 2655–2660, Dec. 1993.

Charles D. Swerdlow et al., "Optimal Electrode Configuration for Pectoral Transvenous Implantable Defibrillator Without an Active Can." *The American Journal Of Cardiology*, vol. 76, pp. 370–374, Aug. 15, 1995.

Gust H. Bardy, et al., "A Simplified, Single–Lead Unipolar Transvenous Cardioversion–Defibrillation System," *Circulation*, vol. 88, No. 2, pp. 543–547, Aug. 1993.

*Primary Examiner*—Scott M. Getzow

[57] ABSTRACT

An external surrogate defibrillation electrode is provided that increases the safety of performing implantation testing of implantable cardioverter-defibrillators. The surrogate electrode has an electrode pad that is attached to the patient's skin. If the implantable cardioverter-defibrillator is not capable of providing a sufficiently high-energy defibrillation shock during the implantation procedure, the surrogate electrode attached to the patient's skin can be electrically connected to the implantable cardioverter-defibrillator, thereby allowing the implantable cardioverter-defibrillator to effectively apply a rescue shock to the patient.

17 Claims, 3 Drawing Sheets

SYSTEM HAVING A SURROGATE DEFIBRILLATION ELECTRODE FOR TESTING IMPLANTABLE CARDIOVERTER-DEFIBRILLATORS DURING IMPLANT

BACKGROUND OF THE INVENTION

This invention relates to the testing of implantable cardioverter-defibrillators.

Implantable cardiac devices, such as pacemakers and implantable cardioverter-defibrillators are well known. Typically, implantable cardiac devices contain sensing circuitry for monitoring the various heartbeat signals produced by a patient's heart. Implantable cardiac devices with sensing circuitry can analyze the patient's heartbeat signals to determine whether electrical pulses should be applied to the heart. For example, pacemakers can determine whether a patient's heart is beating to slowly and therefore needs to be stimulated with pacing pulses. Implantable cardiac devices that have cardioversion and defibrillation capabilities are known as implantable cardioverter-defibrillators (ICDs). ICDs can generate and apply shocks to the patient's heart when an abnormal heart condition such as fibrillation is detected.

In order for an ICD to operate properly after it has been implanted in the patient, the physician implanting the device must ensure that there is a sufficient safety margin between patient's defibrillation threshold and the output of the device. To determine the patient's defibrillation threshold, the physician induces fibrillation in the patient's heart. Once the heart is in fibrillation, the physician applies defibrillation shocks of various energies to determine how strong the shocks must be to defibrillate the patient's heart.

This testing procedure has traditionally involved the use of a dummy ICD can and an external defibrillator system analyzer (DSA). The physician implants the defibrillation coil lead in the patient's heart and places the dummy device in the same location in which the ICD is to be implanted (typically in a left pectoral pocket). After inducing fibrillation, the DSA is used to apply test defibrillation shocks to the heart.

Increasingly, however, physicians have been using what is known as the pro se testing technique, in which an ICD suitable for permanent implantation in the patient is used in place of the dummy device. The ICD itself generates the defibrillation shocks used to determining the defibrillation threshold. Pro se testing is attractive, because it avoids the need to provide a defibrillator system analyzer and a sterile dummy device.

However, there has been a slightly greater risk associated with pro se testing than with traditional testing methods, because the DSA is no longer available to provide a backup rescue shock through efficient internal electrodes. In the event that the ICD is unable to generate a defibrillation shock of sufficient energy to terminate fibrillation, the patient must be defibrillated using a conventional external defibrillator.

What is therefore needed is a way in which to increase the safety of performing pro se ICD implantation testing.

SUMMARY OF THE INVENTION

In accordance with the principles of the present invention, methods and apparatus are provided for increasing the safety of implantation of implantable cardioverter-defibrillators (ICDs) using an external surrogate defibrillation electrode. The surrogate electrode has an electrode pad that is attached to the patient's skin. The pad may be made of a conductive adhesive gel and may have a surface area in the range of about 10–1000 cm$^2$.

If the ICD is not capable of providing a sufficiently high-energy defibrillation shock during the implantation procedure using the normal defibrillation electrodes, the surrogate electrode attached to the patient's skin can be electrically connected to the implantable cardioverter-defibrillator, thereby allowing the ICD to apply a successful rescue shock to the patient. The surrogate electrode effectively reduces the defibrillation threshold for the patient, by increasing the surface area over which the defibrillation shock is applied. Because the defibrillation threshold energy is lower than it would be with a conventional electrode arrangement, pro se implantation testing is safer than it would be using only standard electrodes.

One way in which to interconnect the surrogate electrode and ICD is to use a standard DF–1 pin. Such a pin allows the surrogate electrode to be conveniently attached to a variety of ICDs having standard defibrillation electrode sockets. If an ICD of the two-port header type is used, a titanium pouch can be provided that fits around the exterior of the ICD. The surrogate electrode is connected to ICD using the pouch.

In order to isolate the surrogate electrode from the ICD during normal pro se testing, a switch may be provided on the lead connecting the ICD and surrogate electrode. When the switch is placed in the open position, the physician can test the patient's defibrillation threshold. Defibrillation test shocks are usually applied between a coil electrode in the patient's right ventricle and the can of the ICD. If desired, additional internal defibrillation electrodes may be provided such as a superior vena cava (SVC) electrode or a subcutaneous patch.

If it is necessary to apply a rescue shock to the patient because the ICD is unable to defibrillate the patient at its maximum output using the normal internal defibrillation electrodes, the physician can close the switch, thereby connecting the surrogate electrode to the ICD. The ICD can then apply rescue defibrillation shocks to the skin of the patient with the surrogate electrode in parallel with the internal electrodes. The rescue shocks are effective, because the addition of the surrogate electrode to the defibrillation configuration lowers the defibrillation threshold of the patient's heart.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which.

DETAILED DESCRIPTION OF THE PREFERRED EMBODIMENTS

Figure 1:
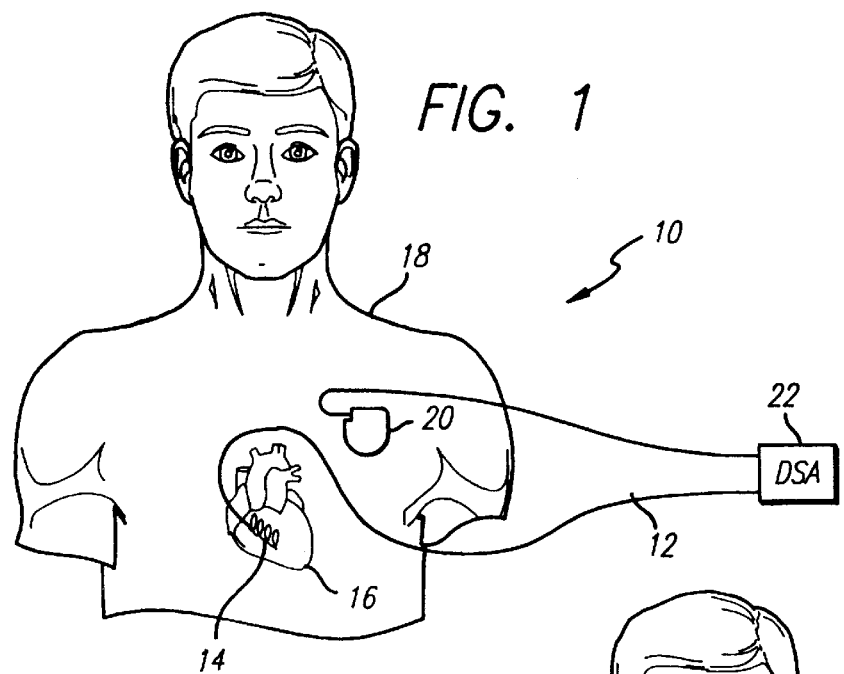
FIG. 1 is a diagram of a conventional testing arrangement in which a defibrillator system analyzer and dummy can are used to determine the defibrillation threshold of a patient's heart.

A typical system 10 for implantation testing of an implantable cardioverter-defibrillator (ICD) is shown in FIG. 1. (As defined herein, the term implantable cardioverter-defibrillator or ICD refers to any type of implantable cardiac device with cardioversion or defibrillation capabilities.) A transvenous lead 12 having a coil electrode 14 is positioned in the right ventricle of the heart 16 of a patient 18. A dummy can 20, which is a metal titanium shell of the same size as the ICD to be implanted, simulates the ICD and is positioned in the left pectoral pocket. The dummy can 20 and the coil electrode 14 are connected to an external defibrillator system analyzer (DSA) 22.

During the implantation procedure, the patient's heart 16 is fibrillated using standard techniques. The DSA 22 is then used to deliver a defibrillation test shock through the coil electrode 14 and the dummy can 20 to defibrillate the heart 16. For purpose of illustration, assume that the ICD to be implanted has a 27 joule maximum output for delivering defibrillation shocks. If the patient is successfully defibrillated with a 17 joule test shock, then the ICD can be permanently implanted in the patient, because the current clinical practice is to allow at least a 10 joule safety margin between the patient's defibrillation threshold and the maximum defibrillation shock output of the ICD.

If the defibrillation threshold is determined to be between 17 joules and 27 joules, the physician will typically add a third electrode and possibly a fourth electrode to reduce the defibrillation threshold. Adding additional electrodes can reduce the defibrillation threshold to approximately one half of the value of the defibrillation threshold for shocks applied between coil 14 and can 20. Most commonly the third electrode is added in the superior vena cava (SVC), because it is a simple venous access position from the left pectoral region. The fourth electrode is typically added to the patient's left side as a subcutaneous patch or an array.

If the defibrillation threshold is greater than 27 joules, the DSA 22 is able to defibrillate the patient by delivering a high energy rescue shock (e.g., about 40–50 joules). This is possible even though the rescue shock energy exceeds the maximum power output of the ICD to be implanted. The rescue shock capability of the DSA 22 ensures that the physician will be able to defibrillate the heart 16.

Using the DSA 22 to apply test shocks and to provide a rescue shock capability prior to implantation of an ICD is generally satisfactory. However, the pro se implantation process, in which the ICD itself generates test shocks to determine the patient's defibrillation threshold, does not require the use of the DSA 22 or the dummy can 20. Eliminating the DSA 22 is advantageous, because the DSA 22 is a complex and expensive piece of equipment, which can be costly to maintain. Eliminating the dummy can 20 is advantageous, because there is always some risk associated with introducing a foreign object such as the dummy can 20 into a sterile surgical environment. Pro se testing in conjunction with ICD implantation are therefore becoming increasingly popular.

Figure 2:
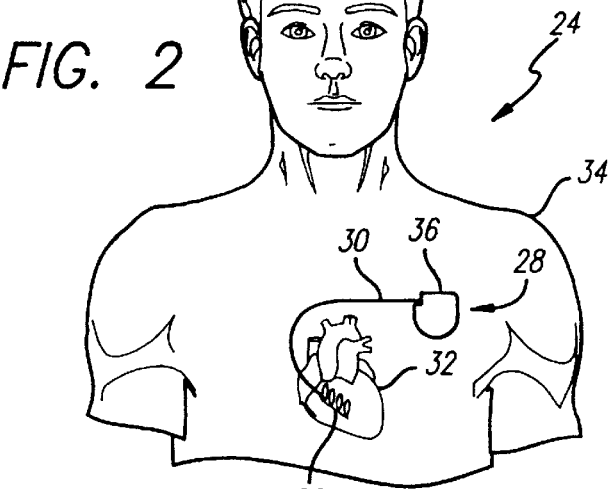
FIG. 2 is a diagram of a conventional implantation testing arrangement.

A typical ICD implantation system 24 is shown in FIG. 2. A first defibrillation electrode is formed by a coil electrode 26, connected to an ICD 28 via a lead 30. The coil electrode 26 is implanted in the right ventricle of the heart 32 of a patient 34. A second defibrillation electrode is formed by the can 36 of the ICD 28. The ICD 28 is implanted in the left pectoral pocket of the patient 34. A physician can control the operation of the ICD 28 using a programmer 38. The programmer 38 and the ICD 28 communicate telemetrically (i.e., via wireless communications).

To determine the patient's defibrillation threshold of the patient 34, the physician induces fibrillation, e.g., by using the programmer 38 to direct the ICD 28 to apply an appropriate shock to the heart 32. The ICD 28 attempts to defibrillate the heart 32 by generating a defibrillation shock. The ICD 28 can be configured to generate such a defibrillation shock automatically or at the direction of the physician.

For purpose of illustration, assume that the ICD 28 has a 27 joule maximum output for delivering defibrillation shocks. A typical first shock energy generated by the ICD 28 to defibrillate the heart 32 is 17 joules. If the patient 34 is reliably defibrillated with 17 joule shocks, then the pectoral pocket can be stitched over and the implantation procedure completed. If the defibrillation threshold is between 17 and 27 joules, then a 27 joule backup second shock will work. Additional electrodes can be used to reduce the threshold, such as an SVC electrode or a subcutaneous patch. Alternatively, the physician could replace the ICD 28 with an ICD having a higher output capacity.

However, in some cases the ICD 28 is incapable of defibrillating the heart 32, even at the maximum available shock energy of 27 joules. Although this occurs relatively infrequently (i.e., less than 1% of the time), when it does occur it creates an emergency situation. The patient 34 can only be defibrillated using external defibrillation equipment of the type commonly used by paramedics. Using this type of defibrillation equipment is not considered to be as safe as using the DSA and dummy can arrangement of FIG. 1.

Figure 3:
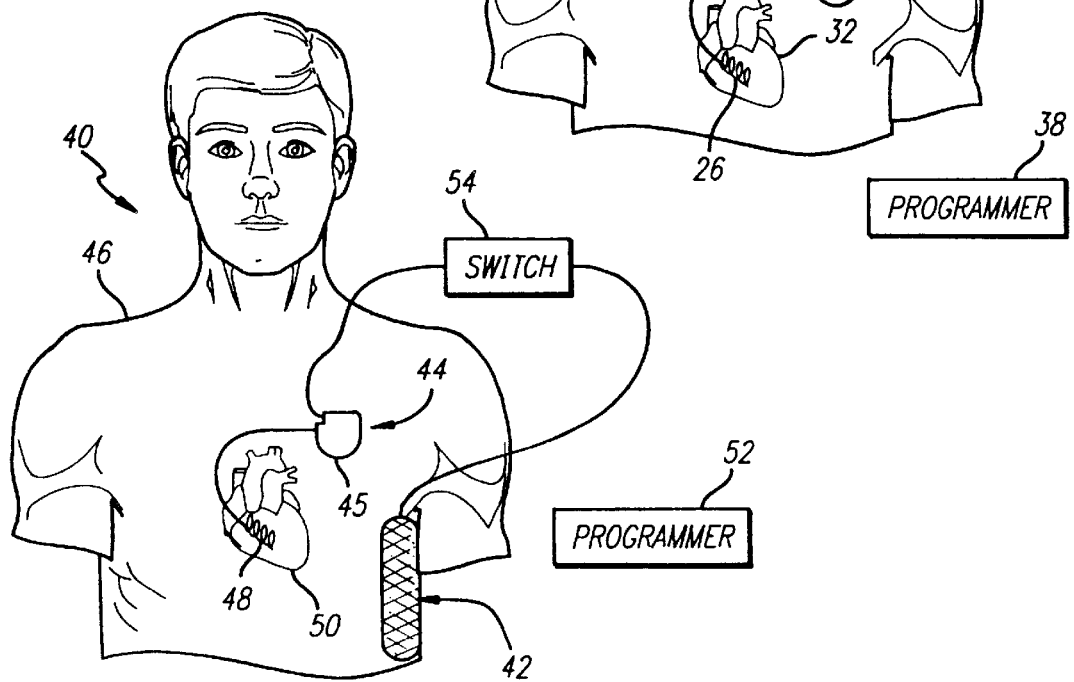
FIG. 3 is a diagram of an implantation testing arrangement in accordance with the present invention.

In accordance with the present invention, an ICD implantation system 40 is provided that increases the safety of the ICD implantation process. As shown in FIG. 3, the system 40 involves the use of an external surrogate electrode 42 connected to an ICD 44 that is implanted in the patient 46. The ICD 44 is preferably an ICD of the type suitable for pro se ICD implantation testing. The ICD 44 applies shocks to the heart 50 via a first defibrillation electrode formed by a coil electrode 48 in the right ventricle of the heart 50 and a second defibrillation electrode formed by the can 45 of the ICD 44. The operation of the ICD 44 can be directed by the physician using a programmer 52, which communicates with the ICD telemetrically (i.e., via wireless communications). The surrogate electrode 42 is connected to the skin of the patient 46, and is used by the ICD 44 to apply rescue defibrillation shocks to the patient 46 when the ICD 44 is unable to defibrillate the heart 50 using the coil electrode 48 and the can 45 of the ICD 44.

Preferably, the physician can electrically connect the surrogate electrode 42 to the ICD 44 by closing a switch 54. With the switch 54 open, ICD 44 can generate test defibrillation shocks to determine the defibrillation threshold of the heart 50. With the switch 54 closed, the surrogate electrode 42 enhances the capacity of the ICD 44 to defibrillate the heart 50 by lowering the effective defibrillation threshold, as when additional internal electrodes such as an SVC electrode or subcutaneous patch electrode are used. As a result, if the ICD 44 is unable to defibrillate the heart 50 by applying the maximum available shock energy to the heart 50 using the coil electrode 48 and the can 45 of the ICD 44, the physician can close the switch 54 and thereby connect the surrogate electrode 42 to the ICD 44. Using system 40 therefore allows the physician to more effectively apply a rescue shock to the patient 46, without using external defibrillator equipment.

Figure 4:
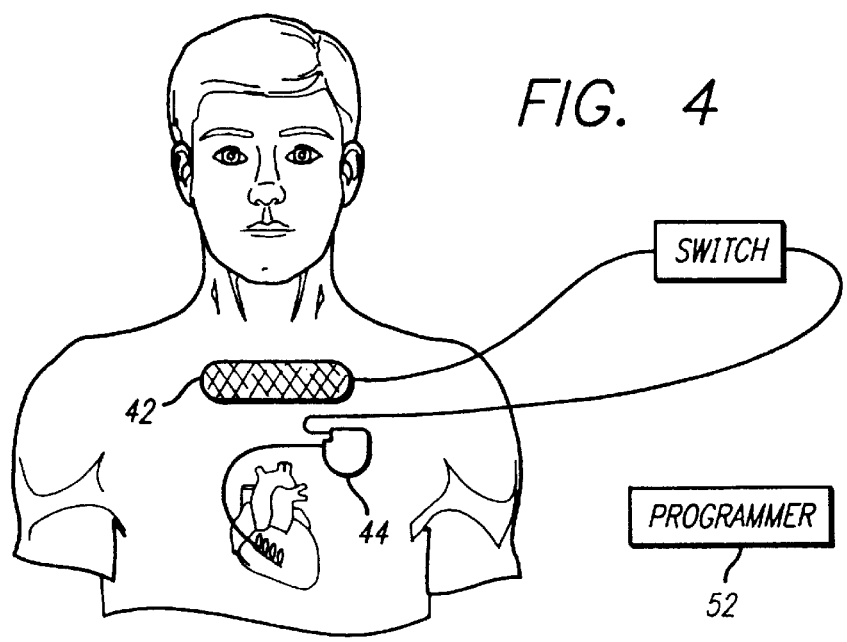
FIG. 4 is a diagram of an implantation testing arrangement in accordance with the present invention showing an alternate location for the external surrogate electrode.

The surrogate electrode 42 can be attached to the body of the patient 46 on the patient's left side, or may be attached to the patient across the top of the chest, as shown in FIG. 4. Although the arrangement of FIG. 4 may better simulate the electric fields that would be generated with an SVC electrode, care should be taken to keep the surrogate electrode 42 away from any conventional backup external defibrillator patches that are used.

Figure 5:
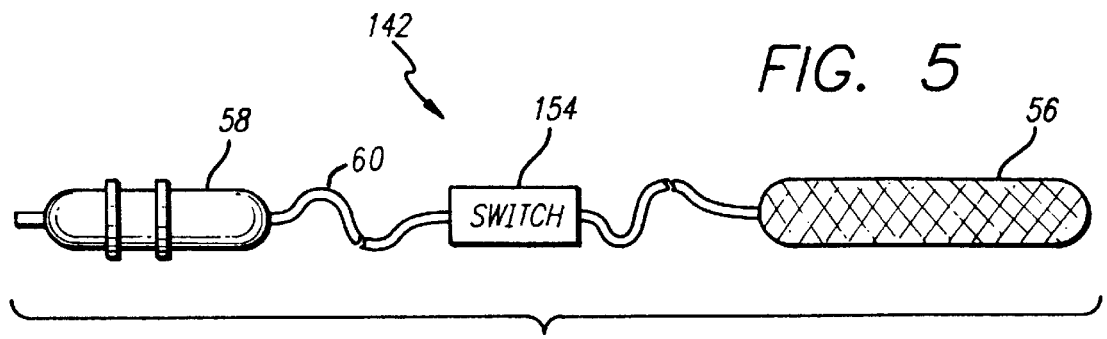
FIG. 5 is a diagram of a surrogate defibrillation electrode in accordance with the present invention.

A suitable surrogate electrode assembly 142 is shown in FIG. 5. An electrode pad 56 is preferably formed from an adhesive gel having a sodium chloride or silver/silver chloride component to provide conduction, such as conventionally used for other types of external electrodes. The concentration of the sodium chloride or silver/silver chloride component is preferably less than that used with conventional external defibrillator electrodes, which are intended to withstand much larger shock energies than the surrogate electrode 142. The area of the electrode pad 56 may be in the range of about 10–1000 cm$^2$. To best simulate a typical field generated by an implantable electrode system, the electrode pad preferably is longer than it is wide (e.g., having a length to width ratio in the range of about 2:1 to 5:1). Alternatively, the pad 56 could be circular to simulate a subcutaneous patch.

The electrode pad 56 is connected to a standard DF-1 pin 58 via a cable 60 and a switch 154. The DF-1 standard defines the defibrillation connection pin used in most contemporary ICDs, so providing the DF-1 pin 58 allows the electrode pad 56 to be electrically coupled to the header of most ICDs. Typically, the header on an ICD has a DF-1 standard pin and also has a pace/sense lead connection (IS-1 standard) for connecting to a cardiac lead used for providing pacing pulses and for monitoring cardiac signals. For defibrillation, the standard header has one DF$^+$ port to which the coil electrode 48 (FIG. 3) is connected. (Note that "DF$^+$" refers to polarity, whereas "DF-1" refers to dimensions.) Defibrillation pulses are applied between the DF$^+$ port and two DF$^-$ ports connected in parallel with the can 45 (FIG. 3). If either an SVC electrode or a subcutaneous patch is provided to lower the defibrillation threshold, such an electrode is connected to one of the DF$^-$ ports. The surrogate electrode 142 is also connected to one of the available DF$^-$ ports during the ICD implantation procedure, so that a rescue shock can be applied to the heart 50 (FIG. 3), if needed. Without the surrogate electrode 142, such a rescue shock might prove ineffective, even at the maximum output of the ICD 44 (FIG. 3).

During an ICD implantation procedure using the surrogate electrode 42 (FIG. 3), the switch 54 (FIG. 3) is kept open and the patient fibrillated and defibrillated with a moderate energy shock (e.g., 17 joules if the maximum output of the ICD 44 is 27 joules). If defibrillation is successful with the 17 joule shock, the surrogate electrode 42 is unplugged from the ICD 44 and the implantation procedure is completed. If the defibrillation threshold is between 17 and 27 joules, additional electrodes such as an SVC electrode or a subcutaneous patch can be added to reduce the defibrillation threshold as needed. In the event that the ICD 44 is unable to defibrillate at its maximum output of 27 joules, the physician closes switch 54, which allows the ICD 44 to apply a rescue defibrillation shock to the heart 50 (FIG. 3) via the surrogate electrode 42 attached to the skin of the patient 46.

Figure 8:
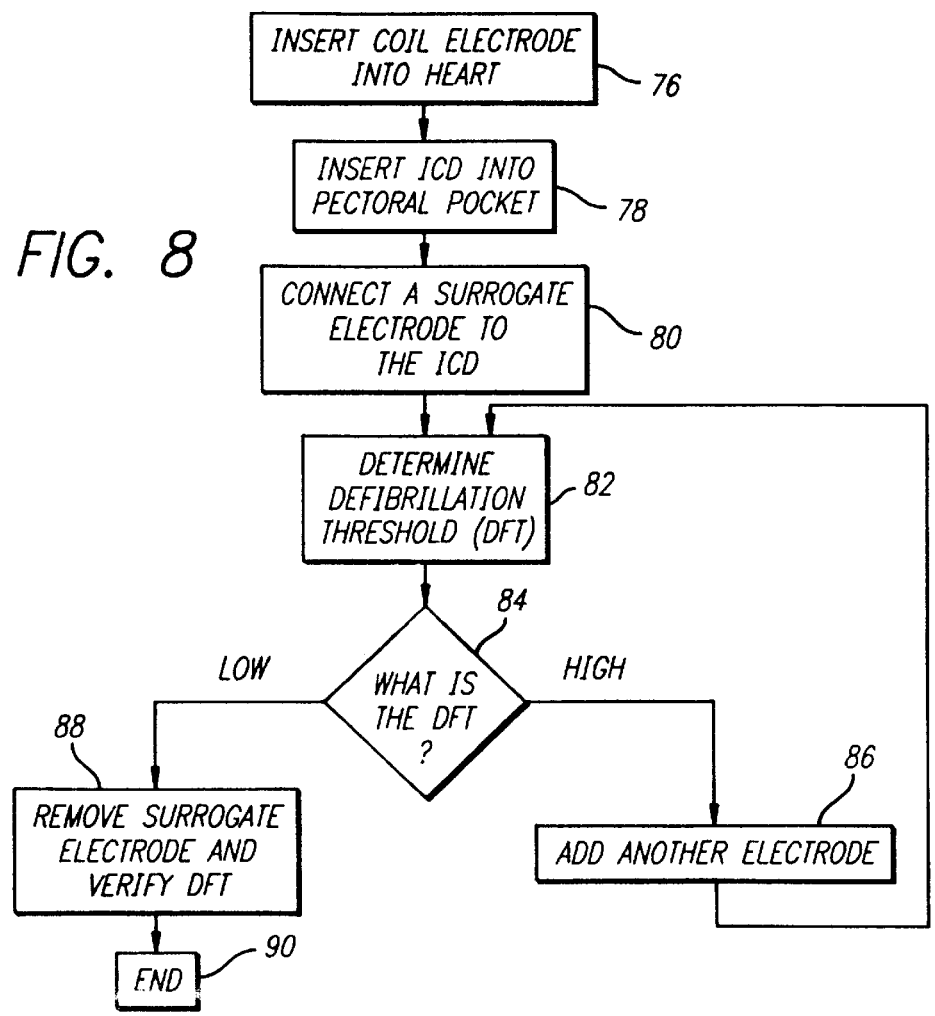
FIG. 8 is a flowchart of steps involved in implantation using a surrogate defibrillation electrode in accordance with the present invention.

In an alternative embodiment, the surrogate electrode is used without a switch, as shown in FIG. 8.

Some ICDs are provided with a two-port header having a single DF$^+$ port in addition to the pace/sense port. (The can serves as the only DF$^-$ connection.) Defibrillation shocks are applied between the DF$^+$ port connected to the coil electrode 48 (FIG. 3) and the can of the ICD 44 (FIG. 3). No DF$^-$ ports are available for the surrogate electrode 42. Although no DF$^-$ ports are available for additional electrodes (such as an SVC electrode or a subcutaneous patch), the small size afforded by the two-port header is sometimes desirable.

Figure 6:
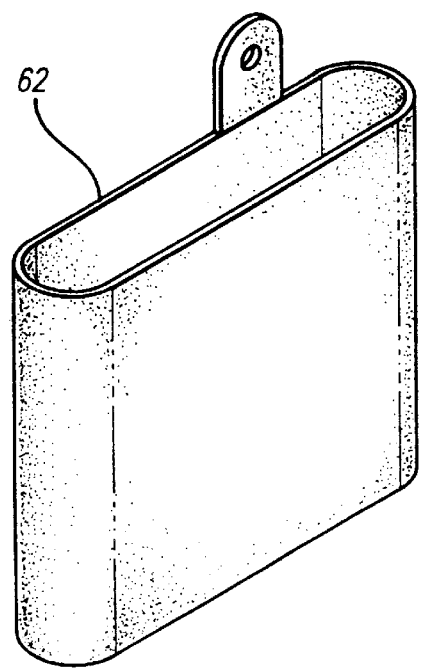
FIG. 6 is a diagram of a pouch for connecting a surrogate electrode to the ICD can in accordance with the present invention.
Figure 7:
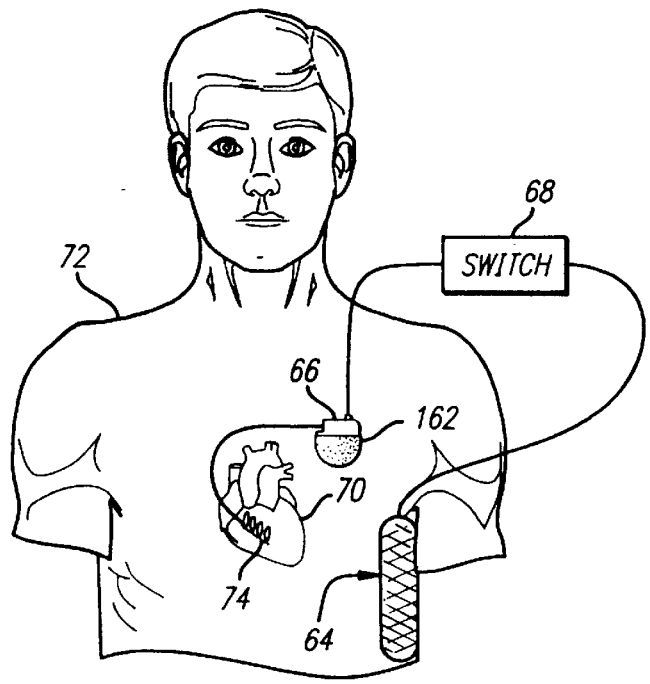
FIG. 7 is a diagram of an implantation testing arrangement using the pouch of FIG. 6 in accordance with the present invention.

The surrogate defibrillation electrode 42 (FIG. 3) can be connected to an ICD having a two-port header by using a pouch 62, such as shown in FIG. 6. The pouch 62 is preferably made of titanium and is the same shape as a standard two-port header ICD. As shown in FIG. 7, a two-port header ICD 66 is placed in a pouch 162 during the ICD implantation procedure. A surrogate electrode 64 is connected to a tab 66 of the pouch 162. A switch 68 is used to connect the surrogate electrode 64 to the ICD 66. Defibrillation shocks are applied to the heart 70 of the patient 72 between a coil electrode 74 and the can of the ICD 66. The pouch 162 electrically connects the surrogate electrode 64 to the can of the ICD 66, so that if it is necessary to apply a rescue shock to the patient 72, the physician can close the switch 68.

Steps involved in ICD implantation using a surrogate electrode without a switch are shown in FIG. 8. At step 76, the physician surgically implants the coil electrode (48 or 74) into the patient's heart (50 or 70). At steps 78 and 80, the ICD is inserted into a pectoral pocket and the ICD is connected to a surrogate electrode. If the ICD has a DF$^-$ port on the header, the surrogate electrode is plugged into the header. If the ICD has a two-port header, a pouch (such as the pouch 62 of FIG. 6) is used to connect the surrogate electrode to the ICD. The defibrillation threshold is determined at step 82.

Because the surrogate electrode is connected to the ICD, the effective defibrillation threshold of the heart is reduced (e.g., by approximately half) from what it would otherwise be. The reduction in the effective threshold value makes it safer to perform pro se implantation testing than if no surrogate electrode were used, because rescue shocks are more likely to be effective. The reduction is taken into account at test 84, where it is determined whether the defibrillation threshold is high or low. For example, if a defibrillation threshold of less than 17 joules is required when no surrogate electrode is in place, the presence of the surrogate electrode will necessitate a defibrillation threshold of less than 8.5 joules (17 joules÷2).

If the defibrillation threshold is found to be high at test 84, another electrode (such as an SVC electrode or a subcutaneous patch electrode) is added at step 86 and the defibrillation threshold determination step 82 is repeated. If the defibrillation threshold is found to be low at test 84, the physician removes the surrogate electrode at step 88. In addition, a verification shock is preferably applied at step 88, at an energy level that is scaled up appropriately to compensate for the removal of the surrogate electrode. For example, if the defibrillation threshold was determined to be 5 joules at step 82 (and the surrogate electrode is of a type previously determined to reduce effective thresholds by half)

then the verification shock preferably has an energy of 10 joules. If verification at step 88 is successful, the ICD implantation procedure is completed at step 90. An alternative to the process shown in FIG. 8 is to use a switch to isolate the surrogate electrode during defibrillation threshold testing, as described in connection with FIG. 3.

One skilled in the art will appreciate that the present invention can be practiced by other than the described embodiments, which are presented for the purposes of illustration and not of limitation, and the present invention is limited only by the claims that follow.

What is claimed is:

1. A system for testing implantable cardioverter-defibrillators during implant, the system having an implantable cardioverter-defibrillator means for applying rescue cardioversion-defibrillation shocks to the heart of a patient in conjunction with implantation of the implantable cardioverter-defibrillator means, the system comprising:
    first electrode means for implant in the heart;
    second electrode means for positioning adjacent said heart;
    the cardioverter-defibrillator means including:
        circuitry means connected to the first electrode means and the second electrode means, the circuitry means for applying cardioversion-defibrillation shocks to the heart between the first electrode means and the second electrode means for determining the defibrillation threshold of the heart during implantation of the implantable cardioverter-defibrillator means;
        removable external surrogate electrode means for temporary attachment to the skin of the patient and for detachable connection to the implantable cardioverter-defibrillator means in parallel with the second electrode means during implantation of the implantable cardioverter-defibrillator means; and
        switch means for electrically connecting the external surrogate electrode means to the implantable cardioverter-defibrillator means for applying a rescue shock from the implantable cardioverter-defibrillator means between the external surrogate electrode means attached to the skin of the patient and the first electrode means during implantation of the implantable cardioverter-defibrillator means wherein the external surrogate electrode means and the switch means include means for detaching the external surrogate electrode means and the switch means from the implantable cardioverter-defibrillator means.

2. The system of claim 1, wherein the first electrode means is a coil electrode.

3. The system of claim 1, wherein the external surrogate electrode means comprises a conductive gel adhesive pad.

4. The system of claim 1, wherein the second electrode is an implantable cardiac device can and wherein the external surrogate electrode is connected to a pouch into which the implantable cardiac device can is placed to form an electrical connection with the external surrogate electrode.

5. The system of claim 1, wherein the external surrogate electrode means has an area in the range of 10 $cm^2$ to 1000 $cm^2$.

6. A method for applying rescue defibrillation shocks to the heart of a patient during implantation of an implantable cardiac device having cardioverter-defibrillator capabilities, the implantable cardiac device being connected to a first electrode that is inserted in the heart and a second electrode that is located adjacent the heart, the implantable cardiac device applying defibrillation shocks to the heart between the first electrode and the second electrode for determining the defibrillation threshold of the heart, the method comprising the steps of:
    attaching an external surrogate electrode to the skin of the patient;
    connecting the external surrogate electrode to the implantable cardiac device with a switch, so that the external surrogate electrode is in parallel with the second electrode; and
    closing the switch to electrically connect the external surrogate electrode to the implantable cardiac device to allow the implantable cardiac device to apply a rescue shock between the external surrogate electrode attached to the skin of the patient and the first electrode.

7. The method of claim 6, wherein the first electrode is a coil electrode.

8. The method of claim 6, wherein the external surrogate electrode comprises a conductive gel adhesive pad, a cable connected to the pad, and a DF–1 pin connected to the cable, the step of connecting the external surrogate electrode to the implantable cardiac device comprising the step of plugging the DF–1 pin into a DF–1 port on the implantable cardiac device.

9. The method of claim 6, wherein the second electrode is an implantable cardiac device can and wherein the external surrogate electrode further comprises a pouch, the step of connecting the external surrogate electrode to the implantable cardiac device comprising the step of inserting the implantable cardiac device can into the pouch.

10. The method of claim 6, wherein the external surrogate electrode has an area in the range of 10 $cm^2$ to 1000 $cm^2$.

11. A system for testing implantable cardioverter-defibrillators during implant comprising: an implantable cardiac device having cardioverter-defibrillator capabilities and having an apparatus for applying rescue defibrillation shocks to the heart of a patient during implantation of the implantable cardiac device, the system further comprising:
    a first electrode sized to be inserted in said heart;
    a second electrode configured to be positioned adjacent said heart;
    circuitry connected to the first and second electrodes, the circuitry capable of applying defibrillation shocks to the heart between the first and second electrodes for determining the defibrillation threshold of the heart during implantation of the implantable cardiac device;
    an external surrogate electrode configured to be attached to the skin of the patient and to be connected to the implantable cardiac device in parallel with the second electrode during implantation of the implantable cardiac device; and
    switch means for electrically connecting the external surrogate electrode to the implantable cardiac device to apply a rescue shock from the implantable cardiac device between the external surrogate electrode attached to the skin of the patient and the first electrode during implantation of the implantable cardiac device wherein the external surrogate electrode and the switch means include means for disconnecting said surrogate electrode and the switch means from the implantable cardiac device following implantation of the implanted cardiac device.

12. The system of claim 11, wherein the first electrode is a coil electrode.

13. The system of claim 11, wherein the external surrogate electrode comprises a conductive gel adhesive pad.

14. The system of claim 11, wherein the implantable cardiac device has a can and wherein the second electrode comprises said implantable cardiac device can and wherein the external surrogate electrode is connected to a pouch into which the implantable cardiac device can is placed to form an electrical connection between the implantable cardiac device can and the external surrogate electrode.

15. The system of claim 11, wherein the external surrogate electrode has an area in the range of 10 cm$^2$ to 1000 cm$^2$.

16. A system for testing implantable cardioverter-defibrillators during implant comprising: an implantable cardiac device having cardioverter-defibrillator capabilities and having an apparatus for applying rescue defibrillation shocks to the heart of a patient during implantation, the system further comprising:

a first electrode sized to be inserted in the heart;

a second electrode configured to be positioned adjacent the heart;

circuitry connected to the first and second electrodes and capable of applying defibrillation shocks to the heart between the first and second electrodes for determining the defibrillation threshold of the heart during implantation;

a surrogate electrode pad attachable to the skin of the patient during implantation of the implantable cardiac device;

means for connecting the surrogate electrode pad in parallel with the second electrode when determining the defibrillation threshold of the heart by applying test shocks between the first electrode and the second electrode; and means for disconnecting the surrogate electrode pad from the second electrode when the defibrillation threshold has been determined.

17. A method for applying rescue defibrillation shocks to the heart of a patient during implantation of an implantable cardiac device having cardioverter-defibrillator capabilities, the implantable cardiac device being connected to a first electrode that is inserted in the heart and a second electrode, the implantable cardiac device applying defibrillation shocks to the heart between the first electrode and the second electrode for determining the defibrillation threshold of the heart, the method comprising the steps of:

attaching a surrogate electrode pad to the skin of the patient;

connecting the surrogate electrode pad in parallel with the second electrode when determining the defibrillation threshold of the heart by applying test shocks between the first electrode and the second electrode, wherein the surrogate electrode pad reduces the effective defibrillation threshold of the heart; and disconnecting the surrogate electrode pad from the second electrode when the defibrillation threshold has been determined.

* * * * *